(12) United States Patent
Sayers et al.

(10) Patent No.: US 9,238,069 B2
(45) Date of Patent: Jan. 19, 2016

(54) METHOD OF SENSITIZING CANCER CELLS TO THE CYTOTOXIC EFFECTS OF DEATH RECEPTOR LIGANDS IN CANCER TREATMENT

(75) Inventors: Thomas Joseph Sayers, Boonsboro, MD (US); Nancy Lynn Booth, Bethesda, MD (US); Curtis J. Henrich, Rockville, MD (US); Alan David Brooks, Frederick, MD (US); Kirk R. Gustafson, Frederick, MD (US); Karen L. Erickson, North Oxford, MA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 16 days.

(21) Appl. No.: 13/516,514

(22) PCT Filed: Dec. 16, 2010

(86) PCT No.: PCT/US2010/060821
§ 371 (c)(1),
(2), (4) Date: Oct. 26, 2012

(87) PCT Pub. No.: WO2011/084623
PCT Pub. Date: Jul. 14, 2011

(65) Prior Publication Data
US 2013/0039883 A1    Feb. 14, 2013

Related U.S. Application Data

(60) Provisional application No. 61/287,139, filed on Dec. 16, 2009.

(51) Int. Cl.
| | | |
|---|---|---|
| *A61K 31/16* | (2006.01) | |
| *A61K 31/568* | (2006.01) | |
| *A61K 45/06* | (2006.01) | |
| *A61K 31/047* | (2006.01) | |

(52) U.S. Cl.
CPC ............... *A61K 45/06* (2013.01); *A61K 31/047* (2013.01); *A61K 31/16* (2013.01); *A61K 31/568* (2013.01)

(58) Field of Classification Search
None
See application file for complete search history.

(56) References Cited

U.S. PATENT DOCUMENTS

| | | |
|---|---|---|
| 2004/0127523 A1 | 7/2004 | Bacopoulos et al. |
| 2007/0190022 A1 | 8/2007 | Bacopoulos et al. |
| 2007/0191490 A1* | 8/2007 | Sebti .............. 514/685 |
| 2008/0207578 A1 | 8/2008 | Chu et al. |

(Continued)

FOREIGN PATENT DOCUMENTS

| | | |
|---|---|---|
| CN | 101 455 672 A | 6/2009 |
| WO | WO 2005/025619 A1 | 3/2005 |
| WO | WO 2007/116404 A2 | 10/2007 |

OTHER PUBLICATIONS

"Withanolides potentiate apoptosis, inhibit invasion, and abolish osteoclastogenesis through suppression of nuclear factor-kB (NF-kB) activation and NF-kB-regulated gene expression" by Ichikawa et al., Mol. Cancer Ther. 5, 1434-45 (2006).*

(Continued)

*Primary Examiner* — Theodore R West
(74) *Attorney, Agent, or Firm* — Leydig, Voit & Mayer, Ltd.

(57) ABSTRACT

Disclosed is a method of enhancing the response of cancer cells in a mammal to treatment with a death receptor ligand, which method comprises contacting the cancer cells with a death receptor ligand in conjunction with an effective amount of a compound described herein, for example, a cucurbitacin (I) or a withanolide (II). Also disclosed is a method of inducing apoptosis in cancer cells in a mammal, comprising contacting the cancer cells with a compound described herein, for example, a cucurbitacin (I) or a withanolide (II) and also contacting the cancer cells with a death receptor ligand, whereby apoptosis is induced in the cancer cells.

14 Claims, 13 Drawing Sheets

(56) References Cited

U.S. PATENT DOCUMENTS

| | | |
|---|---|---|
| 2008/0234244 A1 | 9/2008 | Xie et al. |
| 2009/0088412 A1* | 4/2009 | Wu et al. ..................... 514/175 |
| 2009/0247495 A1 | 10/2009 | Xie et al. |
| 2010/0120885 A1 | 5/2010 | Gronemeyer et al. |

OTHER PUBLICATIONS

"Relationship between Chemical Structure and Antitumor Activity of Wathaferin A Analogues" by Yoshida et al., J. Pharm. Dyn. 2, 92-97 (1979).*

"Combination antibody-based cancer immunotherapy" by Takeda et al., Cancer Sci. 98, 1297-302 (2007).*

"New cytotoxic withanolides from Physalis peruviana" by Lan et al., Food Chem. 116, 562-69 (2009).*

Booth et al., "A cell-based high-throughput screen to identify synergistic TRAIL sensitizers," *Cancer Immunol. Immunother.*, 58: 1229-1244 (2009).

European Patent Office, International Search Report and Written Opinion issued in International Patent Application No. PCT/US2010/060821, pp. 1-15 (Jun. 16, 2011).

Lee et al., "Withaferin A sensitizes TRAIL-induced apoptosis through reactive oxygen species-mediated up-regulation of death receptor 5 and down-regulation of c-FLIP," *Free Radical Biology & Medicine*, 46: 1639-1649 (2009).

Liu et al., "Combined antitumor activity of cucurbitacin B and docetaxel in laryngeal cancer," *European Journal of Pharmacology*, 587: 78-84 (2008).

Molavi et al., "Synergistic antitumor effects of CpG oligodeoxynucleotide and STAT3 inhibitory agent JSI-124 in a mouse melanoma tumor model," *Immunology and Cell Biology*, 86: 506-514 (2008).

* cited by examiner

Cucurbitacin B

Cucurbitacin C

Cucurbitacin E

Cucurbitacin I

Withanolide E

Withanolide S

Renal

Melanoma

Withanolide E

Withanolide S

Psammaplin-A

Bisaprasin

METHOD OF SENSITIZING CANCER CELLS TO THE CYTOTOXIC EFFECTS OF DEATH RECEPTOR LIGANDS IN CANCER TREATMENT

CROSS-REFERENCE TO RELATED APPLICATIONS

This patent application is the national stage of International Patent Application No. PCT/US2010/060821, filed Dec. 16, 2010, which claims the benefit of U.S. Provisional Application 61/287,139, filed Dec. 16, 2009, the disclosures of which are incorporated by reference.

BACKGROUND OF THE INVENTION

One strategy in developing new cancer therapeutics having better toxicity profiles compared with current cytotoxic drugs is to utilize molecularly-targeted therapeutics that selectively target cancer cells versus normal cells and can be used in minimal doses to reduce side effects. Death receptor ligands held initial promise in answering this need because they trigger programmed cell death in their target cancer cells. Two of the best-studied death receptor ligands, Fas ligand and tumor necrosis factor-alpha (TNF-α), have proven to be too toxic for systemic use as anticancer agents in their native forms. However, another death receptor ligand, tumor necrosis factor-α-related apoptosis-inducing ligand, known as TRAIL, and its receptors, has renewed interest in this area of cancer research. Active TRAIL receptors, TR1 (DR4) and TR2 (DR5) are often more highly expressed on cancer cells versus normal cells. Inactive TRAIL "decoy" receptors TR3 (DcR1) and TR4 (DcR2) are sometimes more prevalent on the surface of normal cells. Both DR4 and DR5 transduce death signaling, leading to apoptosis upon binding to TRAIL, whereas DcR1 and DcR2 lack intact intracellular death domain and therefore cannot signal apoptosis despite binding to TRAIL. Instead, DcR1 or DcR2 protects cells from TRAIL-induced apoptosis by competing with DR4 and DR5 for binding to TRAIL. Interestingly, the expression of DcR1 and DcR2 is either downregulated or lost in many types of cancer cells or tissues while DR4 and DR5 expression are maintained in cancer cells or tissues. This inversely related expression pattern for TRAIL receptors may be partly responsible for the selectivity of TRAIL ligand for tumor cells over normal cells, and its ability to preferentially cause apoptotic cell death in cancer cells, may contribute to a more favorable safety profile.

TRAIL ligand exists in two forms: as a type II membrane protein expressed on the surface of certain lymphoid cells, and as a cleaved, soluble protein that is detectable in serum. While the biological roles of TRAIL ligand in vivo have not been fully elucidated, recombinant soluble TRAIL causes apoptosis in sensitive tumor cells but not normal cells. Therefore, various TRAIL ligand formulations have been investigated for their therapeutic efficacy as well as possible toxicity in mice, cynomolgus monkeys, and humans. In response to the poor serum stability of recombinant TRAIL in vivo and in an attempt to create more targeted therapeutics with fewer side effects, humanized agonistic monoclonal TRAIL antibodies, such as mapatumumab and lexatumumab, were developed that have either TR1 (i.e., DR4) or TR2 (i.e., DR5) specificity. Phase I and II clinical trials have been carried out using these antibodies as single agents in patients having solid tumors such as colorectal cancer, non-small cell lung cancer, and non-Hodgkin's lymphomas. The useful in vivo half-lives, good tolerability, low toxicity, and efficacy in promoting stable disease in certain patient groups observed for agonistic monoclonal antibodies to TR1 and TR2 have provided a basis for the expectation that TRAIL-targeted therapies may have broad clinical applicability in the treatment of cancer.

While TRAIL has been reported to successfully target certain tumor cells which are resistant to traditional chemotherapies or radiation, TRAIL resistance has also been widely documented. Indeed, many cancer cells are quite resistant to TRAIL as a single agent. There is an unmet need for the development of sensitizers of the cancer cells to TRAIL, especially those that act in a synergistic manner.

BRIEF SUMMARY OF THE INVENTION

The invention provides a method of synergistically enhancing the response of cancer cells in a mammal to treatment with a death receptor ligand, which method comprises administering to the mammal an effective amount of a cucurbitacin derivative of formula (I):

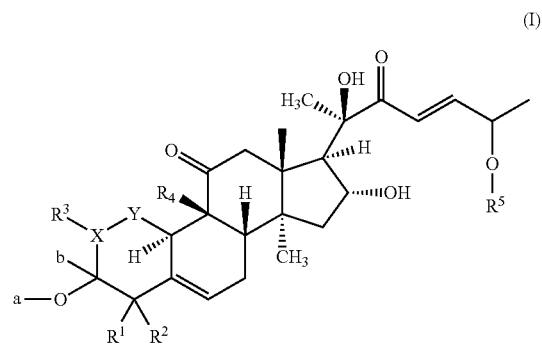

wherein $R^1$ and $R^2$ are independently hydrogen or $C_1$-$C_6$ alkyl, wherein $R^3$ is hydrogen or OH, wherein $R^4$ is methyl or $CH_2OH$, wherein $R^5$ is hydrogen, $C_1$-$C_6$ alkylcarbonyl, or $C_6$-$C_{10}$ arylcarbonyl, wherein a and b are both hydrogen or a-O—C-b forms a C=O, wherein X—Y is $CHCH_2$ or C=CH, with the provisos that (i) when $R^4$ is $CH_2OH$ and X—Y is $CHCH_2$, $R^3$ is hydrogen, and (ii) when $R^5$ is hydrogen and $R^3$ is OH, X—Y is C=CH, and administering an effective amount of a death receptor ligand, whereby a synergistic enhancement of the response is obtained.

The present invention further provides a method of inducing apoptosis in cancer cells in a mammal that are resistant to treatment with a death receptor ligand, comprising administering to the mammal an effective amount of a cucurbitacin derivative of formula (I):

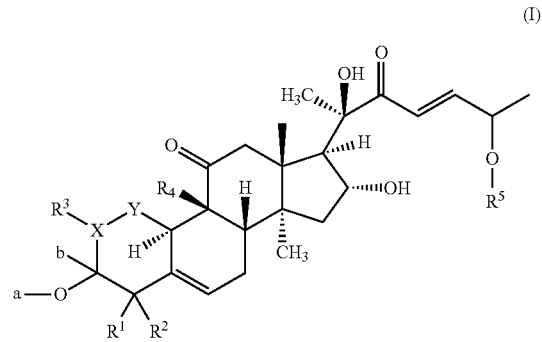

wherein $R^1$ and $R^2$ are independently hydrogen or $C_1$-$C_6$ alkyl, wherein $R^3$ is hydrogen or OH, wherein $R^4$ is methyl or $CH_2OH$, wherein $R^5$ is hydrogen, $C_1$-$C_6$ alkylcarbonyl, or $C_6$-$C_{10}$ arylcarbonyl, wherein a and b are both hydrogen or a-O—C-b forms a C=O, wherein X—Y is $CHCH_2$ or C=CH, with the provisos that (i) when $R^4$ is $CH_2OH$ and X—Y is $CHCH_2$, $R^3$ is hydrogen, and (ii) when $R^5$ is hydrogen and $R^3$ is OH, X—Y is C=CH, and administering an effective amount of a death receptor ligand, whereby apoptosis is induced in the cancer cells.

The present invention further provides a method of synergistically enhancing the response of cancer cells in a mammal to treatment with a death receptor ligand, which method comprises administering to the mammal an effective amount of a withanolide derivative of formula (II):

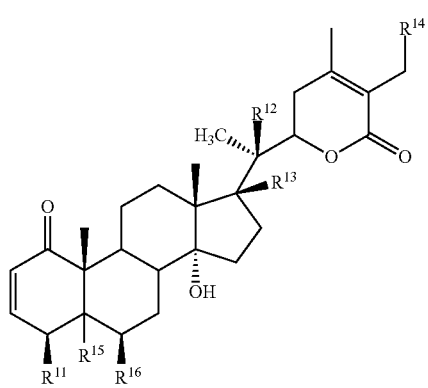

(II)

The present invention further provides a method of inducing apoptosis in cancer cells in a mammal that are resistant to treatment with a death receptor ligand, comprising administering to the mammal an effective amount of a withanolide derivative of formula (II):

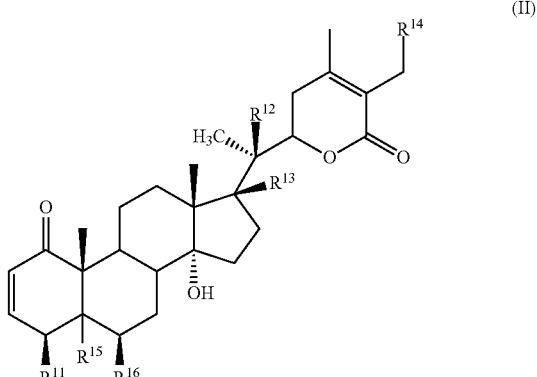

(II)

wherein $R^{11}$, $R^{12}$, $R^{13}$, and $R^{14}$, are independently hydrogen, OH, $C_1$-$C_6$ alkyloxy, or $C_1$-$C_6$ alkylcarbonyl, and wherein $R^{15}$ and $R^{16}$ are both OH or wherein $R^{15}$ and $R^{16}$ together form an epoxy ring, and administering to the mammal an effective amount of a death receptor ligand, whereby apoptosis is induced in the cancer cells.

The present invention further provides a method of synergistically enhancing the response of cancer cells in a mammal to treatment with a death receptor ligand, which method comprises administering to the mammal an effective amount of one of the following compounds of Formula (III) or Formula (IV):

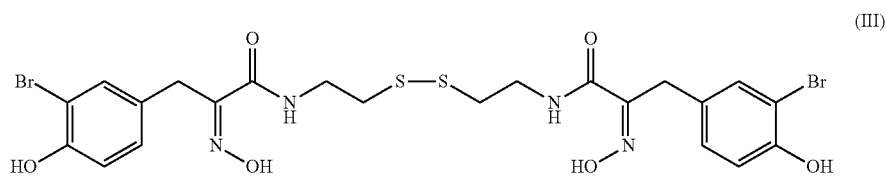

(III)

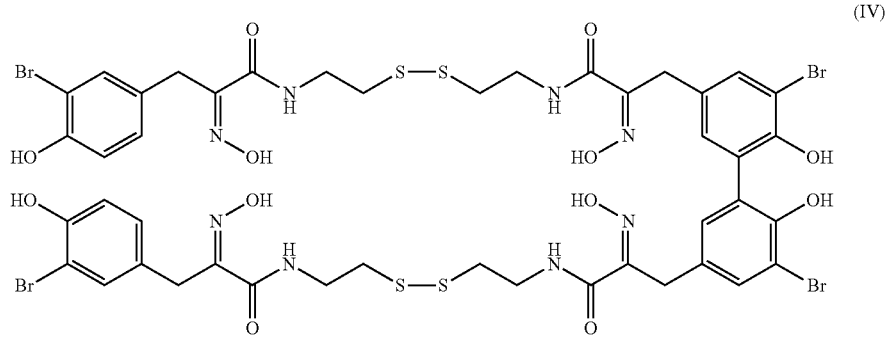

(IV)

wherein $R^{11}$, $R^{12}$, $R^{13}$, and $R^{14}$, are independently hydrogen, OH, $C_1$-$C_6$ alkyloxy, or $C_1$-$C_6$ alkylcarbonyl, and wherein $R^{15}$ and $R^{16}$ are both OH or wherein $R^{15}$ and $R^{16}$ together form an epoxy ring, and administering an effective amount of a death receptor ligand, whereby a synergistic enhancement of the response is obtained.

and administering an effective amount of a death receptor ligand, whereby a synergistic enhancement of the response is obtained.

The present invention further provides a method of inducing apoptosis in cancer cells in a mammal that are resistant to treatment with a death receptor ligand, comprising administering to the mammal an effective amount of one of the following compounds of Formula (III) or Formula (IV):

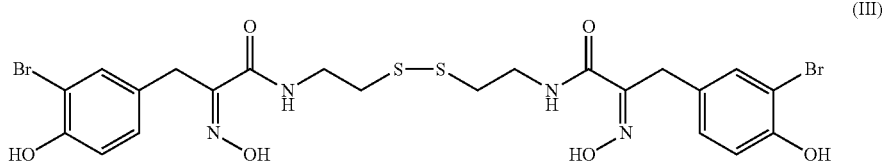

(III)

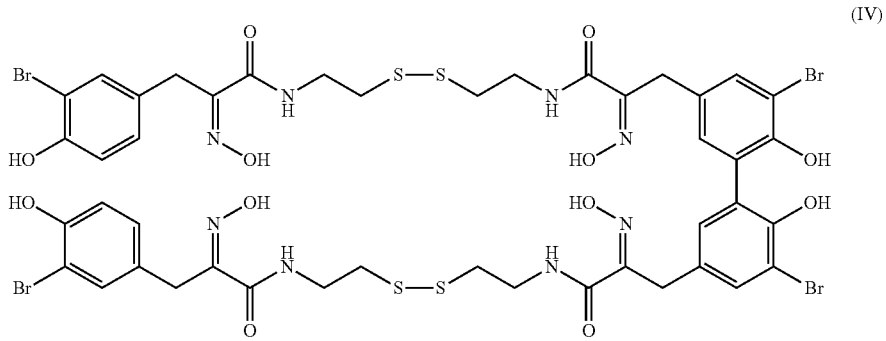

(IV)

and administering to the mammal an effective amount of a death receptor ligand, whereby apoptosis is induced in the cancer cells.

The present invention further provides a method of synergistically enhancing the response of cancer cells in a mammal to treatment with a death receptor ligand, which method comprises administering to the mammal an effective amount of the following compound of Formula (V):

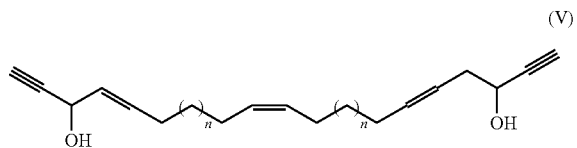

(V)

wherein n is an integer from 1 to 10, and administering an effective amount of a death receptor ligand, whereby a synergistic enhancement of the response is obtained.

The present invention further provides a method of inducing apoptosis in cancer cells in a mammal that are resistant to treatment with a death receptor ligand, comprising administering to the mammal an effective amount of one of the following compounds of Formula (III) or Formula (IV):

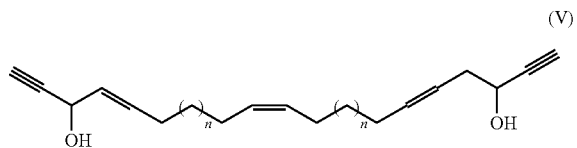

(V)

wherein n is an integer from 1 to 10, and administering to the mammal an effective amount of a death receptor ligand, whereby apoptosis is induced in the cancer cells.

The invention also provides a use of a cucurbitacin derivative of formula (I), a withanolide derivative of formula (II), or one of the compounds of the formulas (III), (IV), or (V), in the manufacture of a medicament for synergistically enhancing the response of cancer cells in a mammal to treatment with a death receptor ligand.

The invention further provides a pharmaceutical kit comprising a first dosage composition comprising a cucurbitacin derivative of Formula (I), and a second dosage composition comprising a death receptor ligand.

The invention further provides a pharmaceutical kit comprising a first dosage composition comprising a withanolide derivative of Formula (II), and a second dosage composition comprising a death receptor ligand.

The invention additionally provides a pharmaceutical kit comprising a first dosage composition comprising a compound of Formula (III), Formula (IV), or Formula (V):

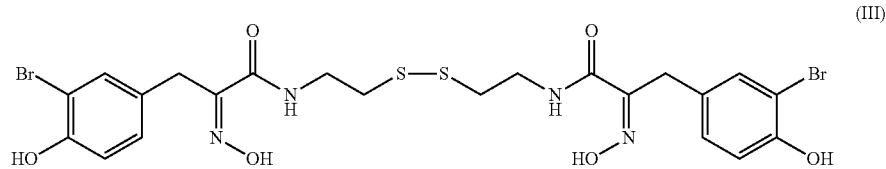

(III)

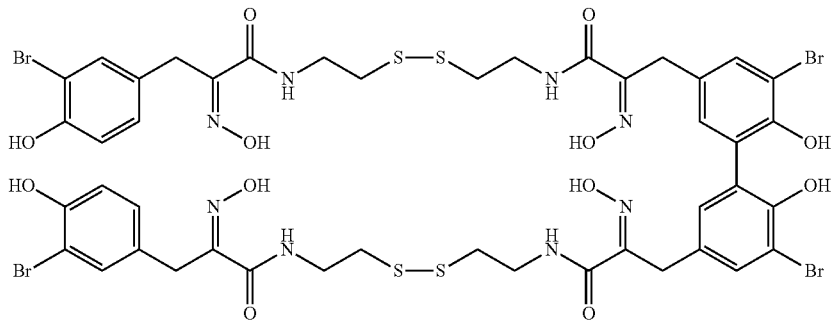

(IV)

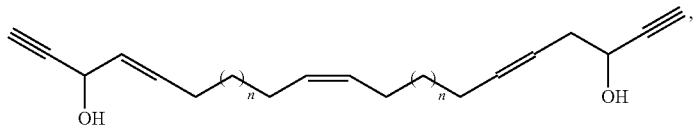

(V)

and a second dosage composition comprising a death receptor ligand.

BRIEF DESCRIPTION OF THE SEVERAL VIEWS OF THE DRAWING(S)

DETAILED DESCRIPTION OF THE INVENTION

Figure 1:
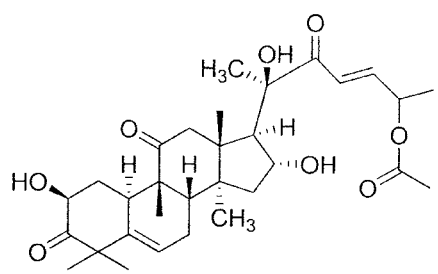
FIG. 1 depicts the structures of cucurbitacins B, C, E, and I.
Figure 1:
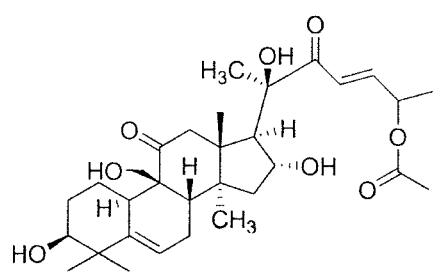
Figure 1:
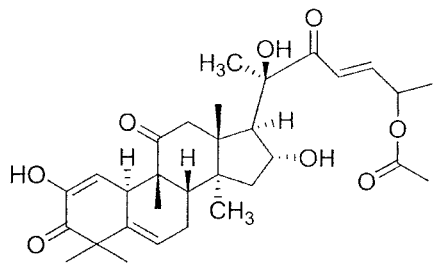
Figure 1:
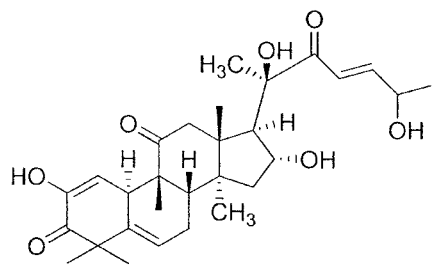

The invention provides a method of synergistically enhancing the response of cancer cells to treatment with a death receptor ligand, which method comprises contacting the cancer cells with an effective amount of a death receptor ligand in conjunction with an effective amount of a sensitizer, whereby a synergistic enhancement of the response is obtained. The sensitizer is a cucurbitacin, a withanolide, or a compound of Formula (III), Formula (IV), or Formula (V) as described herein.

Desirably, the sensitizer is a synergistic TRAIL-sensitizer.

By "enhancing the response" is meant that the death receptor ligand has a greater effect (e.g., at least a 5% increase, at least a 10% increase, at least a 20% increase, at least a 30% increase, at least a 40% increase, at least a 50% increase, at least a 60% increase, at least a 70% increase, at least an 80% increase, etc.) in the presence of the sensitizer than in the absence of the sensitizer. Since the death receptor ligand causes apoptosis in cancer cells, if a sensitizer sensitizes the cancer cells to the death receptor ligand, the cancerous cell is more susceptible to apoptosis triggered by the death receptor ligand, thereby making it more likely to experience programmed cell death as a result of use of the inventive method.

The invention also provides a method of inducing apoptosis in cancer cells in a mammal, comprising (a) sensitizing the cancer cells by contacting the cancer cells with a sensitizer, and (b) contacting the cancer cells with an effective amount of a death receptor ligand, wherein apoptosis is induced in the cancer cells.

In an embodiment, the sensitizer is a cucurbitacin. In some embodiments, the cucurbitacin has the structure recited in Formula (I):

(I)

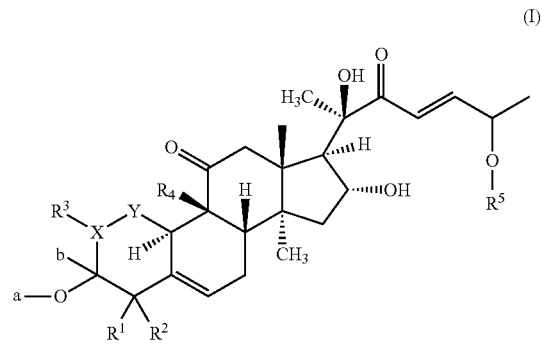

wherein $R^1$ and $R^2$ are independently hydrogen or $C_1$-$C_6$ alkyl, wherein $R^3$ is hydrogen or OH, wherein $R^4$ is methyl or $CH_2OH$, wherein $R^5$ is hydrogen, $C_1$-$C_6$ alkylcarbonyl, or $C_6$-$C_{10}$ arylcarbonyl, wherein a and b are both hydrogen or a-O—C-b forms a C=O, wherein X—Y is $CHCH_2$ or C=CH, with the provisos that (i) when $R^4$ is $CH_2OH$ and X—Y is $CHCH_2$, $R^3$ is hydrogen, and (ii) when $R^5$ is hydrogen and $R^3$ is OH, X—Y is C=CH.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise $4n+2\pi$ electrons, according to Hückel's Rule.

The terms "alkylcarbonyl" and "arylcarbonyl" refer to a substituent of the structure: RC=O wherein alkylcarbonyl contains as an R group an alkyl as defined herein and arylcarbonyl contains as an R group an aryl as defined herein.

In preferred embodiments, the cucurbitacin is selected from the group consisting of cucurbitacin B, cucurbitacin C, cucurbitacin E, and cucurbitacin I having the structures depicted in FIG. 1.

The cucurbitacins are a group of bitter-tasting, highly oxygenated, mainly tetracyclic, triterpenic plant substances derived from the cucurbitane skeleton. M. Miro, Phytother. Res. 8, 159-168 (1995). Natural cucurbitacins are predominantly found in the family Cucurbitaceae which contain some 900 species in about 100 genera, many familiar as the wild gourds, squash, cucumbers, and melons of Cucurblta, Cucumis, Citrullus, Marah, Echinocystis, Lagenaria, Scyos, Ecballium, and Bryonia. At least 100 species in 30 genera have been shown to contain cucurbitacins. Traditionally, the cucurbitacins are arbitrarily divided into twelve categories, incorporating cucurbitacins A-T. A typical purification process involves extraction of the cucurbitacins in plants or plant extracts by non-polar solvents such as hexane, petroleum ether and ethanol followed by separation of cucurbitacins by column chromatography or high-performance liquid chromatography using silica gel columns (U.S. Pat. No. 5,925,356).

In an embodiment, the sensitizer is a withanolide. In some embodiments, the withanolide is a withanolide derivative having the structure recited in Formula (II):

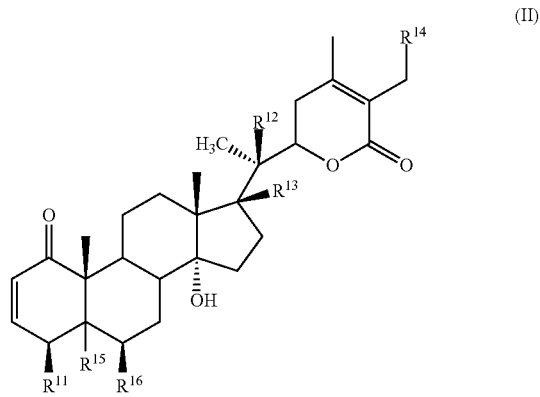

(II)

wherein $R^{11}$, $R^{12}$, $R^{13}$, and $R^{14}$, are independently hydrogen, OH, $C_1$-$C_6$ alkyloxy, or $C_1$-$C_6$ alkylcarbonyl, and wherein $R^{15}$ and $R^{16}$ are both OH or wherein $R^{15}$ and $R^{16}$ together form an epoxy ring.

Figure 2:
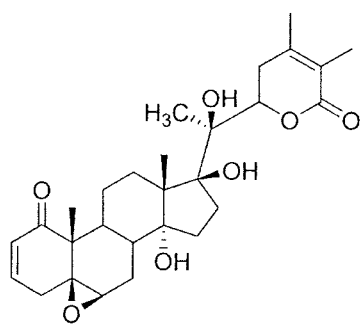
FIG. 2 depicts the structures of withanolides E and S.
Figure 2:
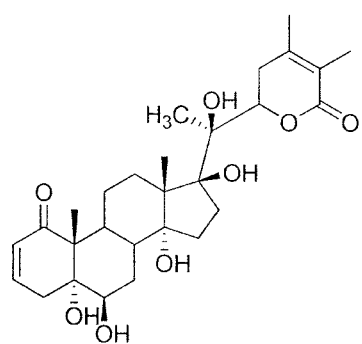
Figure 3:
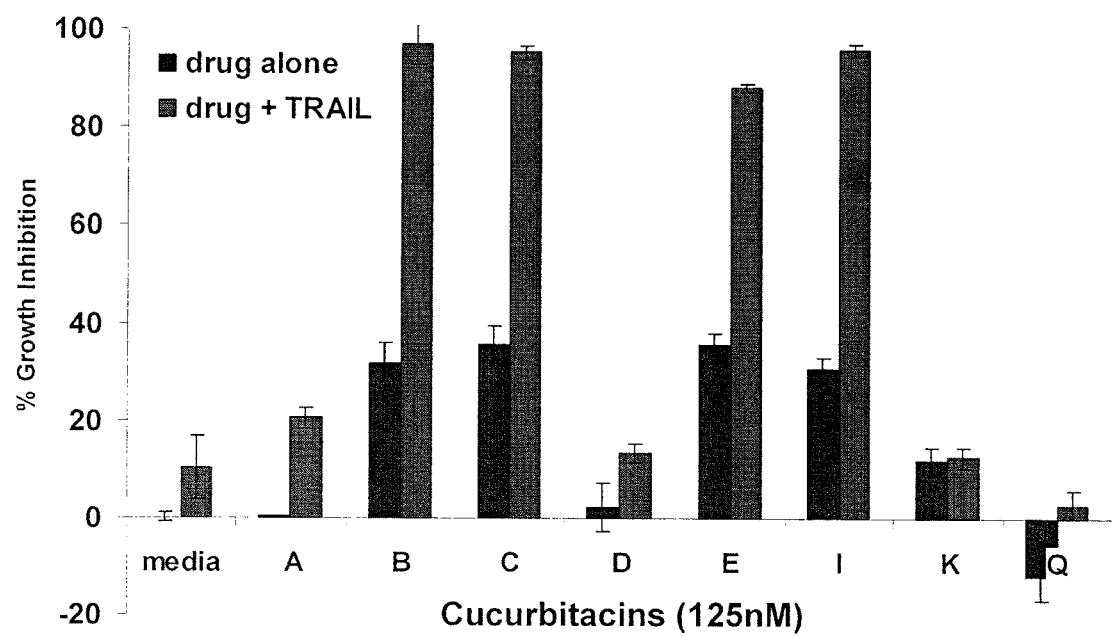
FIG. 3 depicts activation of TRAIL-induced apoptosis by various cucurbitacins. Cucurbitacins A, B, C, D, E, I, K, and Q were assayed at a concentration of 125 nM to determine their effect on percent growth inhibition of ACHN renal cancer cells alone and in the presence of 200 ng/mL of TRAIL.
Figure 4:
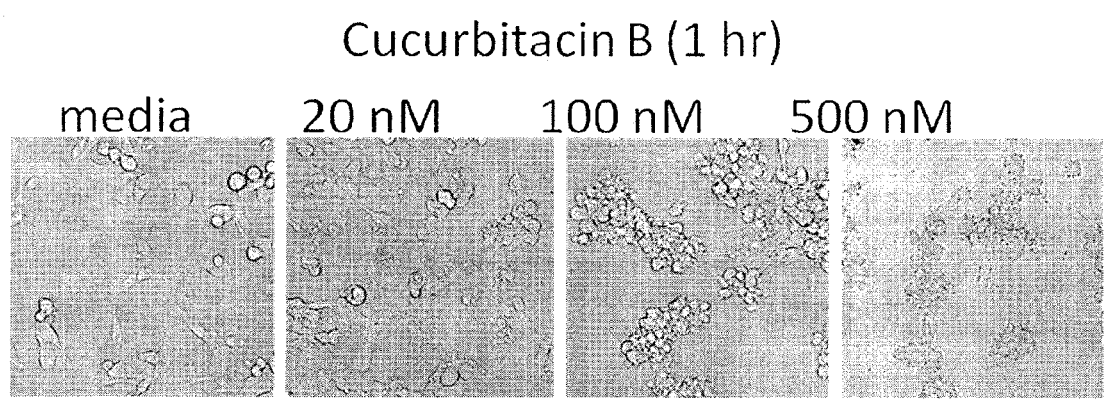
FIG. 4 depicts the effect on cucurbitacin B on ACHN renal cancer cell morphology at concentrations of 20 nM, 100 nM, and 500 nM.

In preferred embodiments, the withanolide is withanolide E or withanolide S having the structures depicted in FIG. 2.

The withanolides are polyoxygenated steroids constructed from the ergostane skeleton. See, for example, Studies in Natural Products Chemistry, Volume 20: Structure and Chemistry (Part F), Atta-ur-Rahman, ed., New York: Elsevier Science, Inc., (1998). Withanolides are constituents of *Withania somnifera*, a tree of the genus *Withania* of the family Solanaceae, which is distributed in India and South Africa. Among the constituents of *Withania somnifera* are withanolides such as withaferin A, sitoindosides I-X, withanolide N, withanolide O, withanolide D, withanolide E, withanolide P, withanolide S, withanolide Q, withanolide R, withanolide G, withanolide H, withanolide I, withanolide J, withanolide K, withanolide U, and withanolide Y, as well as alkaloids such as cuscohygrine, anahygrine, tropine, pseudotropine, anaferine, dl-isopellatierine, 3-tropyltigloate, withasomine, visamine, withaninine, withanine, pseudowithaninine, 3-alpha-tigloyloxytropane, and choline.

In certain embodiments, the sensitizer is a conjugate of cystamine. In preferred embodiments, the sensitizer is a symmetrical bromotyrosine conjugate of cystamine, or a dimer thereof. In more preferred embodiments, the sensitizer is psammaplin A having Formula (III) or bisaprasin having Formula (IV):

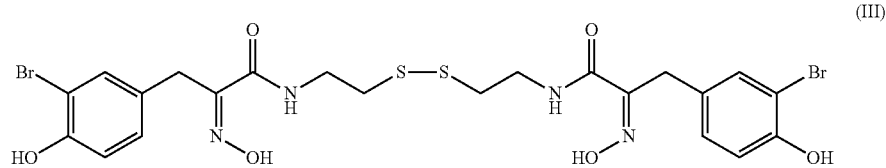

(III)

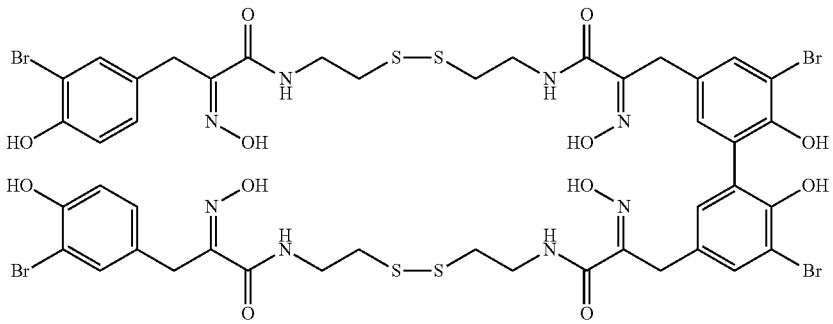

(IV)

In certain embodiments, the sensitizer is a symmetric disubstituted olefin having terminal 3-hydroxy-pent-4-ene-2-yne moieties. In preferred embodiments, the sensitizer is a compound of the formula (V):

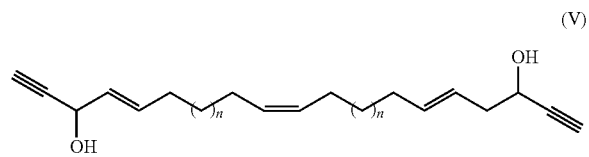

(V)

wherein n is an integer of 1 to 10, preferably 2 to 9, for example, 3, 4, 5, 6, 7, or 8, and more preferably 7 or 8.

As used herein, the term "synergistic" refers to a combination of compounds of the invention and/or a combination of a compound or compounds of the invention and another therapy (e.g., a prophylactic or therapeutic agent), including one which has been or is currently being used to prevent, manage or treat a disorder (e.g., a proliferative disorder or cancer), which combination is more effective than the additive effects of the individual compounds or therapies. A synergistic effect of a combination of therapies (e.g., a combination of prophylactic or therapeutic agents) can permit the use of lower dosages of one or more of the therapies and/or less frequent administration of the therapies to a subject with a disorder (e.g., a proliferative disorder or cancer). The ability to utilize lower dosages of a therapy (e.g., a prophylactic or therapeutic agent) and/or to administer the therapy less frequently can reduce the toxicity associated with the administration of the therapy to a subject without reducing the efficacy of the therapy in the prevention, management or treatment of a disorder (e.g., a proliferative disorder or cancer). In addition, a synergistic effect can result in improved efficacy of agents in the prevention, management or treatment of a disorder (e.g., a proliferative disorder or cancer). Moreover, a synergistic effect of a combination of therapies (e.g., a combination of prophylactic or therapeutic agents) can avoid or reduce adverse or unwanted side effects associated with the use of either therapy alone.

The term "synergistic" is contrasted with the term "additive" in that a combination of an agent having an additive effect and a death receptor ligand exhibits an effect that is simply the sum of the effect produced by the agent and the death receptor when administered individually.

Figure 11:
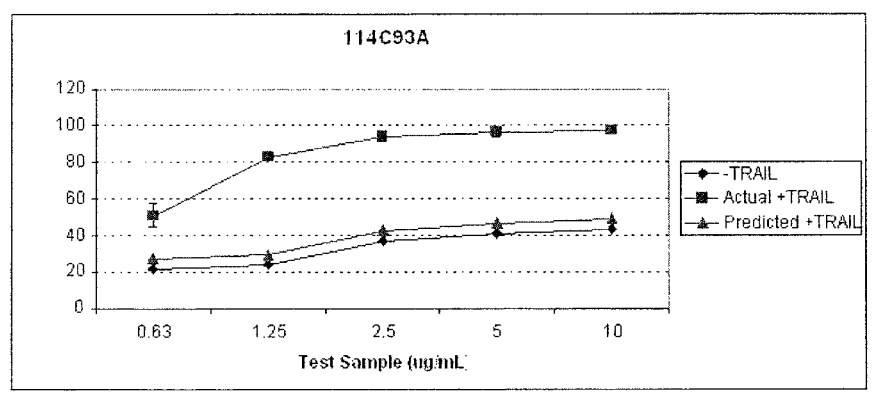
FIG. 11 depicts the dose-response curves for withanolide E and withanolide S in the presence of TRAIL.
Figure 11:
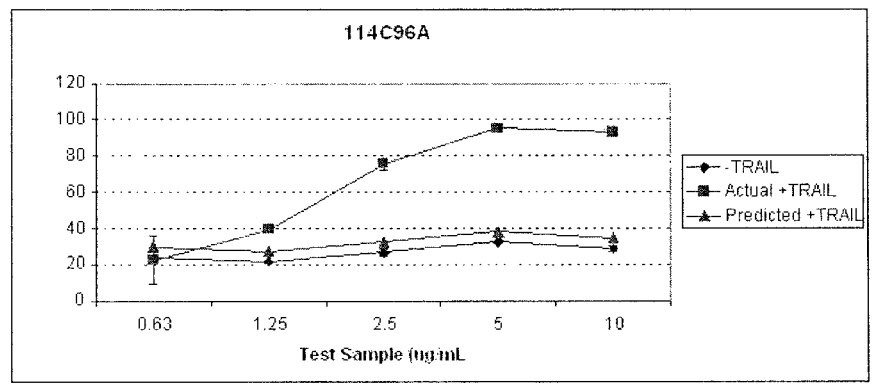
Figure 12:
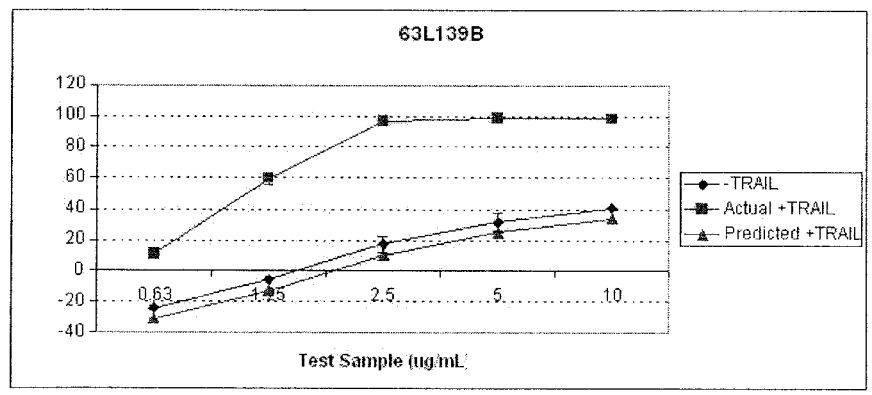
FIG. 12 depicts the dose-response curves for psammaplin A and bisaprasin in the presence of TRAIL.
Figure 12:
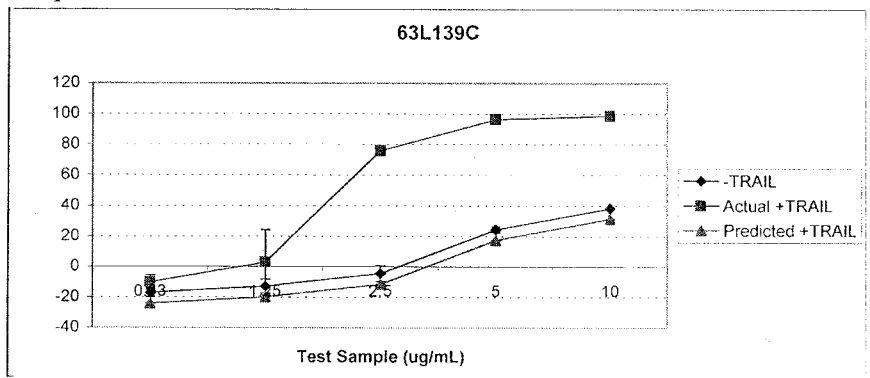
Figure 13:
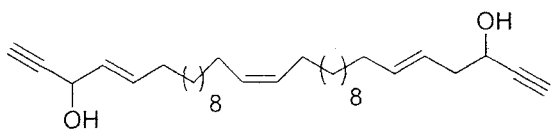
FIG. 13 depicts the dose-response curves for durene and a homolog of durene in the presence of TRAIL.
Figure 13:
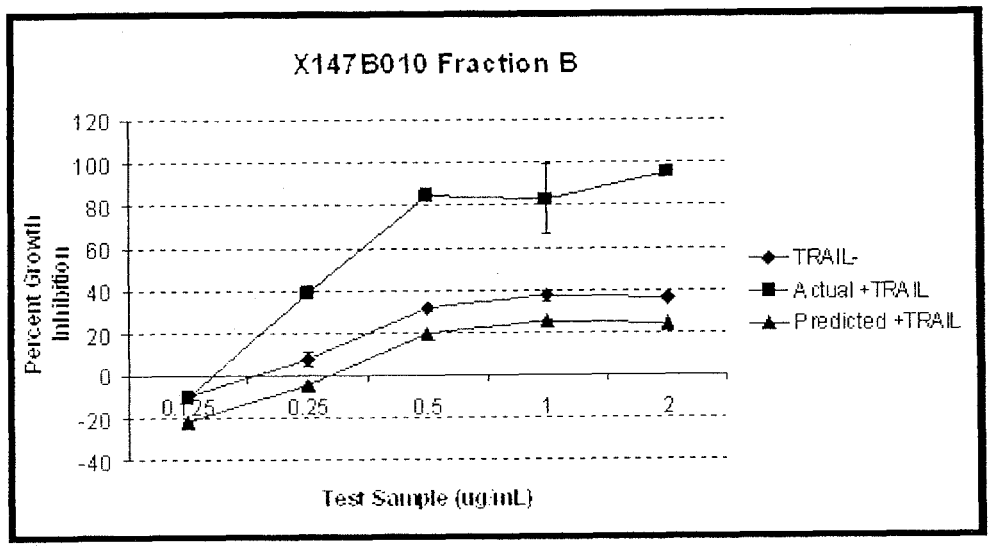
Figure 13:
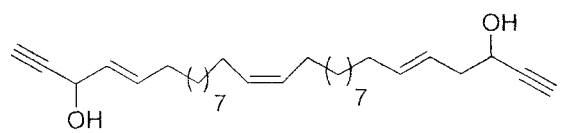
Figure 13:
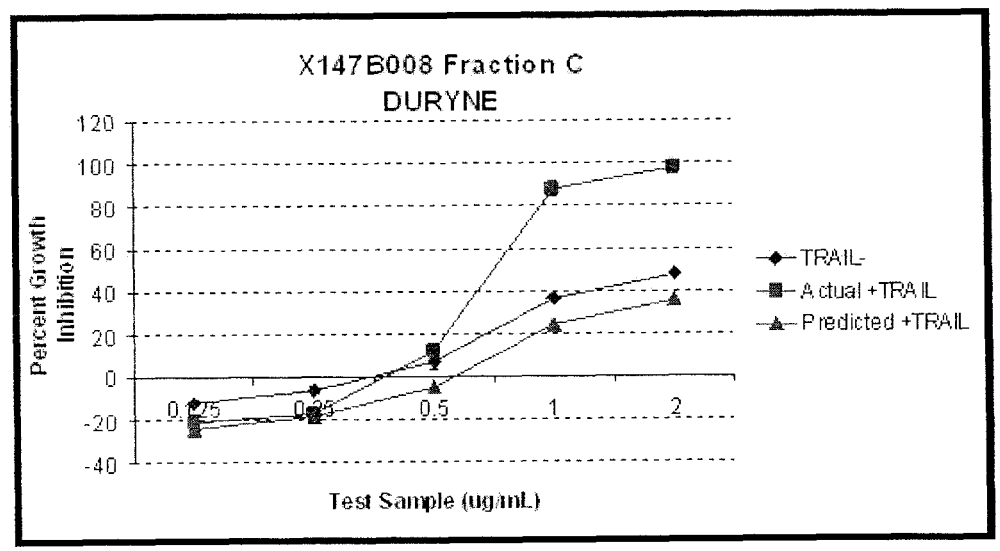

FIG. 11 depicts the dose-response curves for withanolide E and withanolide S in the presence of TRAIL. The y-axis represents percent growth inhibition for ACHN renal cancer cells. The lines labeled "−TRAIL" are the dose-response curves for withanolide E and withanolide S in the absence of TRAIL. The lines labeled "predicted +TRAIL" is the predicted additive percent growth inhibition resulting from addition of the growth inhibition due to withanolide E and withanolide S plus TRAIL. The lines labeled "Actual +TRAIL" is the actual percent growth inhibition determined by the assay. The percent growth inhibition of ACHN renal cancer cells resulting from treatment with both withanolide E and withanolide S in combination with TRAIL is substantially greater than the percent growth inhibition results from treatment with either sensitizer alone or with TRAIL alone, thereby confirming the synergistic response resulting from the combination.

As used herein, the term "death receptor ligand" refers more specifically to a "death receptor agonist" and is intended to mean an agent capable of stimulating by direct or indirect contact the pro apoptotic response mediated by the death-receptors. TRAIL itself binds to DR4 and DR5. An agonist TRAIL receptor antibody would bind to TRAIL receptor and trigger an apoptotic response. In embodiments, the death receptor ligand is selected from the group consisting of TRAIL, TNF-α, FasL, an anti-DR4 antibody, and an anti-DR5 antibody. In preferred embodiments, the death receptor ligand is TRAIL, an anti-DR4 antibody, or an anti-DR5 antibody. In more preferred embodiments, the death receptor ligand is TRAIL.

TRAIL (also referred to as ApoL2) is tumor necrosis factor-α-related apoptosis-inducing ligand and is a widely expressed member of the tumor necrosis factor (TNF) superfamily. TRAIL ligand exists in two forms: as a type II membrane protein expressed on the surface of certain lymphoid cells, and as a cleaved, soluble protein that is detectable in serum. For the purposes of the present invention, soluble recombinant TRAIL is suitable for use and is available from several vendors such as Peprotech, Inc. (Rocky Hill, N.J.). The percent growth reduction in treated cells is thought to be the result of apoptosis induced by the death receptor ligand.

Agonist antibodies directed against the death receptors TRAIL-R1 and/or TRAIL-R2 also can be used in conjunction with the method of the present invention. Exemplary agonist antibodies that may be used in combination with the method of the present invention include those described in U.S. Pat. No. 7,244,429; in U.S. Patent Application Publication Nos. 2007/0179086, 2002/0004227, 2006/0269554, 2005/0079172, 2007/0292411, 2006/0270837, 2006/0269555, 2004/0214235, and 2007/0298039; and in International Patent Publications WO2006/017961 and WO98/51793. Each of these publications is hereby incorporated by reference in its entirety. In addition, anti-DR4 and anti-DR5 antibodies are commercially available from Sigma Aldrich (St. Louis, Mo.) and Enzo Life Sciences (Farmingdale, N.Y.). In preferred embodiments, compounds of the invention are used in combination with one or more of these TRAIL receptor agonist antibodies for the treatment of cancer and other neoplasms.

Examples of suitable antibodies include purified soluble monoclonal antibody which specifically binds TRAIL receptor DR5, wherein said antibody has in vitro cell death-inducing activity in the absence of crosslinking by a secondary antibody and at concentrations less than 1 micromol.g/ml in target cells expressing DR5, and wherein the antibody has in vivo cell death-inducing activity in target cells expressing DR5, and wherein the antibody does not bind TRAIL receptor DR4, DcR1, or DcR2.

Any method known in the art can be used to measure the enhancement of the response to cancer cells to treatment with a death receptor ligand. In addition, any known method known in the art can be used to determine the induction of apoptosis. The Examples section of the present specification describes exemplary methods. For example, the growth inhibition of cancer cells can be determined by measurement of the decrease in cell viability by use of the tetrazolium/formazan assay ("XTT assay") as described in Scudiero et al., *Cancer Res.* 48(17): 4827-4833 (1988), or by use of the sulphorhodamine B protein staining assay ("SRB protein stain") as described in Skehan et al., *J. Natl. Cancer Inst.* 82(13): 1107-1112 (1990) or in Vichai et al., *Nat. Protoc* 1(3): 1112-1116.

The cancer cells in a human can be contacted with a death receptor ligand in conjunction with a sensitizer by administering to the human a formulation containing an effective amount of the sensitizer and a formulation containing the death receptor ligand. In some embodiments, the sensitizer can be present in the same formulation as the death receptor ligand so that the administration can be simultaneous. Any of the sensitizers of the invention can be used in combination with a death receptor ligand, e.g., simultaneously, sequentially, e.g., before or after the death receptor ligand, or cyclically. In some embodiments, it is suitable to administer two or more separate and distinct formulations, one of which contains the sensitizer and the other contains the death receptor ligand. The separate and distinct formulations can be administered simultaneously, or the formulations can be administered separately at different time periods. For example, in preferred embodiments, the formulation containing the sensitizer can be administered about 1 hour (e.g., about 2 hours, or about 3 hours, or about 4 hours, or about 8 hours, or about 24 hours) prior to administration of the formulation containing the death receptor ligand. In preferred embodiments, the death receptor ligand is administered parenterally in the form of a suitable parenteral formulation, while the sensitizer can be administered in the form of any suitable formulation. Suitable formulations include oral, aerosol, nasal, pulmonary, parenteral, subcutaneous, intravenous, intramuscular, intraperitoneal, intrathecal, intratumoral, topical, rectal, and vaginal formulations.

The pharmaceutical composition can be administered parenterally, e.g., intravenously, subcutaneously, intradermally, or intramuscularly. Thus, the invention provides compositions for parenteral administration that comprise a solution or suspension of the sensitizer and/or the death receptor ligand dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, $4^{th}$ ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The sensitizer and/or death receptor ligand may be administered in a physiologically acceptable ampoules in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one sensitizer and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the sensitizer dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The sensitizer, alone or in combination with other suitable components, can be made into aerosol formulations to be administered via inhalation. The compounds are preferably supplied in finely divided form along with a surfactant and propellant. Typical percentages of a sensitizer are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the sensitizer may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the sensitizer, such carriers as are known in the art to be appropriate.

It will be appreciated by one of ordinary skill in the art that, in addition to the aforedescribed pharmaceutical compositions, the sensitizer may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the sensitizer. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired sensitizer can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

"Treating" within the context of the present invention, means an alleviation of symptoms associated with a disorder or disease, or halt of further progression or worsening of those symptoms, or prevention or prophylaxis of the disease or disorder. For example, within the context of treating patients with renal cancer, successful treatment may include a reduction in the proliferation of capillaries feeding the diseased tissue, an alleviation of symptoms related to a cancerous growth or tumor, or a halting in the progression of a disease such as cancer or in the growth of cancerous cells. Treatment may also include administering the pharmaceutical formulations of the present invention in combination with other therapies. For example, the sensitizer and death receptor ligand may be administered before, during, or after surgical procedure and/or radiation therapy. The sensitizer and death receptor ligand can also be administered in conjunction with other anti-cancer drugs and drugs used in antisense and gene therapy. Appropriate combinations can be determined by those of skill in the oncological and medical arts.

"Preventing" within the context of the present invention, refers to a prophylactic treatment of an individual prone or subject to development of a cancer. For example, those of skill in the oncological and medical arts may be able to determine, based on clinical symptoms and patient history, a statistical predisposition of a particular individual to the development of the cancer. Accordingly, an individual predisposed to the development of a cancer may be treated with a sensitizer and death receptor ligand in order to prevent, inhibit, or slow the development of the disease or disorder.

One skilled in the art will appreciate that suitable methods of utilizing a sensitizer and a death receptor ligand and administering the sensitizer and a death receptor ligand to a human for the treatment or prevention of disease states, in particular, cancers responsive to treatment with death receptor ligands (e.g., renal cancers and melanomas) which would be useful in the method of the present invention, are available. Although more than one route can be used to administer the sensitizer and a death receptor ligand, a particular route can provide a more immediate and more effective reaction than another route. Accordingly, the described methods are merely exemplary and are in no way limiting.

The dose of the sensitizer and the dose of the death receptor ligand administered to a mammal, particularly, a human, in accordance with the present invention should be sufficient to effect the desired response. Such responses include reversal or prevention of the bad effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose of the sensitizer and the dose of the death receptor ligand will also be determined by the route, timing and frequency of administration as well as the existence, nature, and extent of any adverse side-effects that might accompany the administration of the dose of the sensitizer and the dose of the death receptor ligand and the desired physiological effect. It will be appreciated by one of skill in the art that various conditions or disease states may require prolonged treatment involving multiple administrations.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the subject can be the unborn offspring of any of the forgoing hosts, especially mammals (e.g., humans), in which case any screening of the subject or cells of the subject, or administration of compounds to the subject or cells of the subject, can be performed in utero.

Suitable doses and dosage regimens can be determined by conventional range-finding techniques known to those of ordinary skill in the art. Generally, treatment is initiated with smaller dosages that are less than the optimum dose of the sensitizer and/or the death receptor ligand. Thereafter, the dosage is increased by small increments until the optimum effect under the circumstances is reached. The present inventive method typically will involve the administration of about 0.01 to about 10 mg, in certain embodiments about 0.1 mg to about 5 mg, and in other embodiments 0.1 mg to about 2 mg, of one or more of the sensitizers and about 0.1 to about 300 mg of the death receptor ligand described above, per kg body weight of the mammal.

The invention also provides a use of a sensitizer compound in the manufacture of a medicament useful in the treatment of cancer, comprising a sensitizer compound in combination with a death receptor ligand. The sensitizer is a cucurbitacin, a withanolide, or a compound of Formula (III), Formula (IV), or Formula (IV) as described herein. The medicament desirably synergistically enhances the response to cancer cells in a mammal to treatment with a death receptor ligand.

The invention further provides a pharmaceutical kit comprising a first dosage composition comprising a sensitizer, and a second dosage composition comprising a death receptor ligand. The sensitizer is a cucurbitacin, a withanolide, or a compound of Formula (III), Formula (IV), or Formula (IV) as described herein. The first and second dosage compositions are individually packaged within each of the pharmaceutical kits.

The pharmaceutical kits of the present invention are preferably identified in print for use in cancer therapy.

In any of the embodiments of the invention, the cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof. The cancer can be any suitable cancer, for example, follicular thyroid carcinoma, colorectal cancer, pancreatic cancer, leukemias, such as myeloid leukemia, prostate cancer, hepatic cancer, hepatocellular carcinoma, cholangiocarcinoma, cervical and ovarian cancer, cancers of glial origin and renal cancer.

In accordance with an embodiment, the methods can be applied to treat patients who are immune compromised, e.g., those who have a reduced p53 function.

The following examples further illustrate the invention but, of course, should not be construed as in any way limiting its scope.

EXAMPLES

Cucurbitacins B, C, E, and I were obtained from Chromadex, Inc. (Irvine, Calif.). Withanolides E and S, and withanone were obtained from Chromadex, Inc. (Irvine, Calif.). Recombinant TRAIL ligand (168 amino acid TNH-homologous extracellular domain) was purchased form Peprotech, Inc. (Rocky Hill, N.J.). 2,3-Bis(2-methoxy-4-nitro-5-sulfophenyl)-5-[(phenylamino)carbonyl]2H-tetrazolium hydroxide (XTT) was provided by the Drug Synthesis and Chemistry Branch, DTP/NCO (Frederick, Md.).

Example 1

This Example illustrates an experimental protocol for assaying sensitivity. On the day prior to an assay, passage 14 to 25 ACHN cells were fed fresh red medium in the morning and harvested after ≥6 h into clear test medium. Cells were seeded at 3,500 cells per well into clear 384-well tissue culture treated plates (BD Biosciences; San Jose, Calif.) in 40 μL total volume of clear test medium using a sterilized gill dispenser (BioTek Instruments, Incl; Winooski, Vt.). Parallel sets of plates (two per library plate, designated "–TRAIL"

and "+TRAIL") were placed in the incubator without stacking and were left to attach to wells overnight (16-20 h).

The next day, test compounds and controls were diluted to 10× final concentration in clear test medium and 5 µL per well was added to each set of assay plates using a Biomek FX-384 equipped with a multichannel pod and Span-8 head (Beckman Coulter, Inc.; Fullerton, Calif.). The following controls were included per individual assay plate: DMSP background (blank); 40 mM bortezomib (final concentration; positive control for +TRAIL plate), and 5 µM sanguinarine chloride (final concentration; positive cytotoxicity control for –TRAIL plate), containing % DMSO matched to test sample content. Plates were returned to the incubator for 4 h±30 min. After presensitization, 5 µL of clear test medium was added per well to the entire +TRAIL plate. Plates were returned to the incubator and incubated overnight (20-21 h).

On the final day, viable cell numbers were assessed using the XTT assay (Scudiero et al., *Cancer Res.* 48(17): 4827-4833 (1988). Plates were allowed to develop for 4-5 h before being read for absorbance at 450 nm on a Wallac Victor 1420 multilabel HTS counter plate reader (Waltham, Mass.).

Percent reduction in cell numbers was calculated for test samples and positive controls based on either untreated (DMSO-only; –TRAIL plate) cells or TRAIL-only treated (+TRAIL plate) cells as negative controls. Percent reduction in cell number was calculated as follows:
–TRAIL plate: % Reduction in cell number (RC)=[(Avg $Abs_{solvent-only\ cells}$–$Abs_{sample}$)/Avg $Abs_{solvent-only\ cells}$]×100, and +TRAIL plate: % RC=[(Avg $Abs_{TRAIL-only\ cells}$–$Abs_{sample}$)/Avg $Abs_{TRAIL-only\ cells}$]×100, wherein Avg Abs=average absorbance and Abs=absorbance.

Two separate Z'-factor quality control parameters were calculated, for –TRAIL and +TRAIL plates, according to the method described in Zhang et al., *J. Biomol. Screen* 4(2): 67-73 (1999). Each plate was subject to two quality control cutoffs to ensure reliability of data: (1) cell controls (either DMSO-only or TRAIL-only) must be ≥1.2 absorbance at 450 nm and (2) calculated Z'-factors for each plate must be ≥0.4 (maximum=1.0).

Initial hits were retested in quadruplicate at the same concentration used in screening to confirm their activity. Confirmation of activity was based on the consistency of the best three out of four test values for each set of results (–TRAIL and +TRAIL), to allow for random variation across plates.

Example 2

This Example illustrates another aspect of the assay. In order to eliminate potential metabolic effects, sulphorhodamine B protein staining ("SRB") was used as an alternative endpoint for the dose-response assays. To determine probable synergistic activity of confirmed hits with TRAIL, a dose-response assay was carried out using the SRB protein staining protocol for cyclotoxicity using the same cell line and similar conditions as those described in Example 1. Controls were combined on each assay plate and included: SRB background absorbance (no cells), untreated (DMSO-only) cells, TRAIL-only cells, cytotoxicity positive control –TRAIL (sanguinarine hydrochloride; one concentration), and synergy positive control +TRAIL (bortezomib; one concentrion plus a dose-response range).

Compound dilutions were prepared in clear test medium and added to cells. A similar protocol and time course as described in Example 1 was employed, except that TRAIL was added to a final concentration of 20 ng/mL and the final overnight incubation took place for 24-25 hours. Cells were fixed to the bottom of the wells by direct addition of 1:1 volume (50 µL) of ice cold 20% (w/v) trichloroacetic acid solution. Plates were incubated at 4° C. for 30-60 min to fix cells and then plates were aspirated and rinsed 5× with deionized water using an Embla 96/384 plate washed (Molecular Devices, Sunnyvale, Calif.), and then allowed to dry at room temperature. Wells were stained for total protein content using 30 µL of SRB (1 g/L in 1% acetic acid) for 1 h at room temperature. Then plates were tapped onto paper towels and allowed to dry at room temperature. Dye was resolubilized by addition of 10 mM TRIZMA base solution (30 µL) and resuspended on a rotary shaker for a few minutes before reading the plates for absorbance at 520 nm using a Safire plate reader (Tecan Group Ltd., Männedorf, Switzerland).

After subtraction of background absorbance (SRB, no cells) from raw data, percent reduction in cell number values for samples were calculated in relation to solvent-only treated cells and this time the effect of the TRAIL reagent alone was determined:
% RC TRAIL=[(Avg $Abs_{solvent-only\ cells}$–$Abs_{TRAIL-only\ cells}$)/Avg $Abs_{solvent-only\ cells}$]×100. Z' factors were calculated similarly as described in Example 1, except that the controls for the +TRAIL portion of the assay were: untreated cells=cells (–TRAIL) and positive control=cells with bortezomib (+TRAIL). Calculations were normalized to untreated cells (–TRAIL) in all instances.

The average value for % RC by TRAIL reagent alone (per plate) was used to generate a "predicted" curve for the expected additive activity of test compounds +TRAIL using the following calculation:

$$\text{Avg \% RC}_{compound(-TRAIL)} + \text{Avg \% RC}_{cells(+TRAIL)} = \text{Predicted \% RC}_{compound(+TRAIL)}.$$

Results were plotted in SigmaPlot as three % RC curves per compound's dose-response: (1) compound/extract effect –TRAIL (cytotoxicity), (2) actual compound effect +TRAIL (synergy effect), and (3) predicted effect of compound +TRAIL (expected additive effect). The results for withanolides E and S are depicted in FIG. 11.

Example 3

This Example illustrates an effect of a sensitizer on production of caspase 8 by cells treated with TRAIL. The Caspase-Glo™ Assay (Promega Corporation, Madison, Wis.) was performed according to the manufacturer's instructions. On the day prior to the assay, passage 14 to 25 ACHN cells were plated at 7000 cells/well in 25 µL clear test medium in white luminescence tissue culture-treated 384-well plates (Corning #3704). Separate plates were used per time point and cells were allowed to attach to plates at 37° C. overnight (15-20 h).

The next day, compounds or DMSO solvent controls were added at 5 µL/well. Clear test media blank or TRAIL (40 nm/mL) was added to cells at 5 µL/well. Plates were returned to the incubator for the appropriate period of time while any zero hour plates were processed immediately. For processing, plates were removed from the incubator, allowed to cool to room temperature for 10 min, enzyme controls were added if appropriate, and then 35 µL of the Glo lysis buffer was added per well (1:1, v:v). Plates were shaken on an orbital rotator for 30 s and then covered with aluminum foil and the luminescence signal was allowed to develop at room temperature for 2-4 h. Plates were read for luminescence on a Wallac Victor 1420 multilabel HTS counter. When background signal had decayed to a stable state, that data set was used (usually 3 h).

Figure 10:
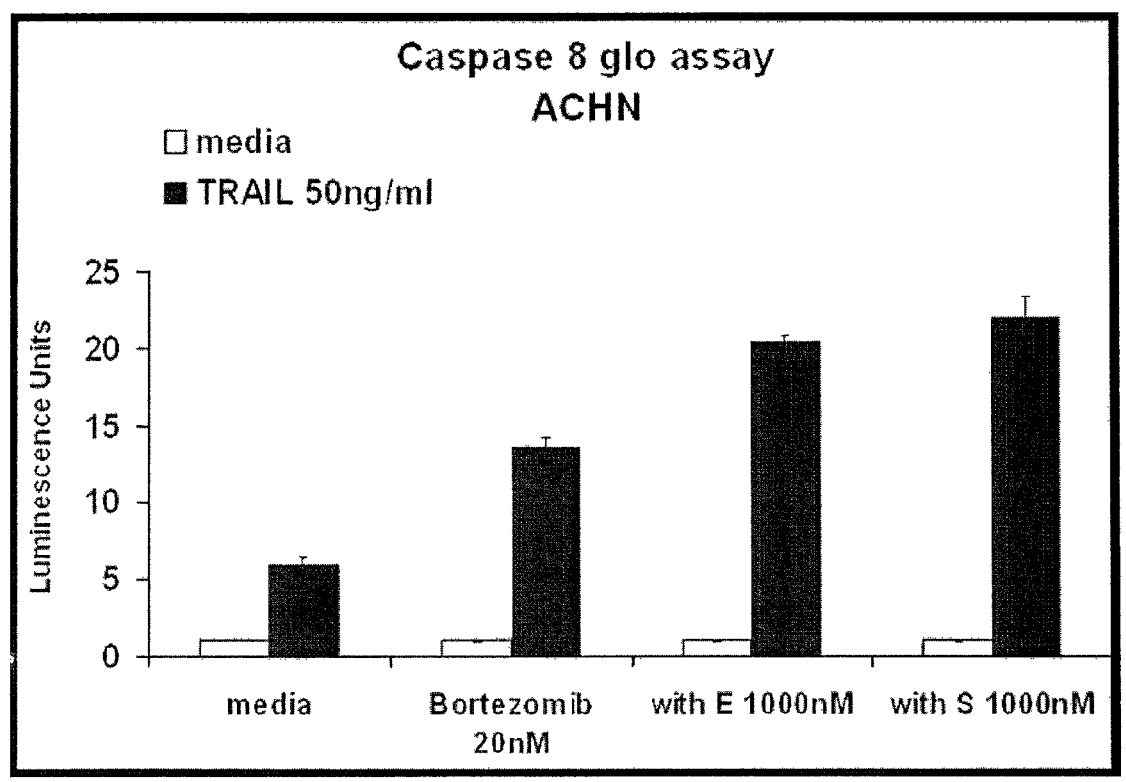
FIG. 10 depicts the activation of caspase-8 in ACHN renal cancer cells by treatment with 20 nM bortezomib, 1000 nM withanolide E, and 1000 nM withanolide S in the presence of 50 ng/mL TRAIL.

The results for withanolide E and withanolide S are depicted in FIG. 10.

Example 4

This Example illustrates cleavage of caspase resulting from treatment of cells with anolides in combination with TRAIL. ACHN cells were seeded into 6-well tissue culture plates at 59.5×14 cells/well in clear test medium and the next day compound was added to a final concentration of 10 μM. Cells were sensitized for 4 h followed by addition of TRAIL to 40 ng/mL final concentration. Cells were harvested in lysis buffer at short intervals after addition of the TRAIL reagent using 165 μL per well. Lysis buffer contained: 50 mM Tris-Cl (pH 8.0), 300 mM NaCl, 5 mM EDTA, 0.5% Triton X-100, 40 μM Z-VAD-FMK, plus one mini-complete protease inhibitor tablet (Roche, Mannheim, Germany) or 100 μL Halt Protease Inhibitor Single-Use Cocktail (Pierce Biotechnology, Inc., Rockford, Ill.) per 6 mL buffer. Lysates were clarified by centrifugation at 4° C. for 15 min at 15,000 rpm and protein content normalized using the bicinchonic acid (BCA) assay (Pierce Biotechnology, Inc.).

Lysates were run under reducing conditions at 20 μg total protein per lane, in NuPAGE 4-12% Bis-Tris gels (1.0 mm×12 well; Invitrogen), using MESS DS running buffer and added antioxidant in the upper chamber. Protein bands were transferred to PVDF membranes using the manufacturer's transfer buffer containing added antioxidant (Invitrogen).

PVDF membranes (0.2 μm pore size) were blocked with 0.1% milk in TBS with 0.5% Tween 20 (0.2 μm filtered) overnight. The blots were then washed 4× with TBS+0.5% Tween 20 then incubated with the primary antibody in TBS+ 5% BSA+0.1% Tween 20 (0.2 μm filtered) overnight. The blots were then washed 4× with TNS+0.5% Tween 20 for 15 min each. Goat anti-rabbit HRP (Pierce Biotechnology, Inc) was added in blocking buffer at 1:500 and incubated with the blots at room temperature for 45 min, the blots were washed 6× with TBS+0.5% Tween 20 for 15 min each, developed with Pierce SuperSignal West Femto Maximum Sensitivity Substrate, and then exposed to Kodak BioMax MR film.

Figure 5:
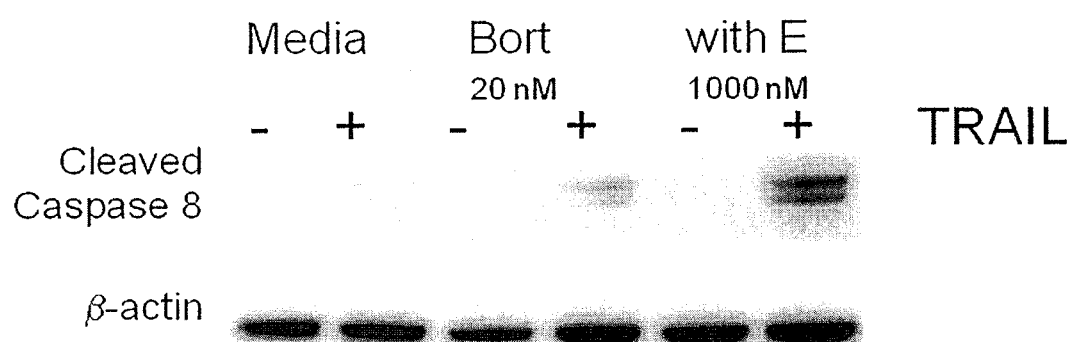
FIG. 5 depicts the effect of cucurbitacin B on caspase-8 activation.
Figure 6:
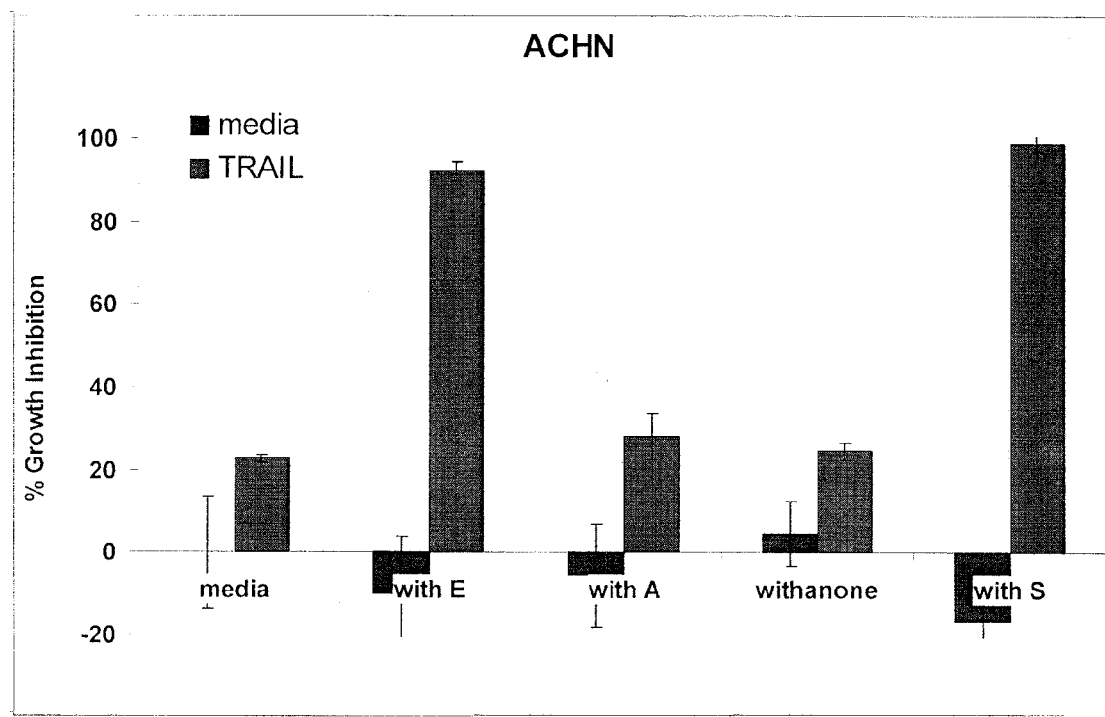
FIG. 6 depicts the percent growth inhibition of ACHN renal cancer cells in the presence of 1000 nM of withanolides A, E, and S, and withanone, in the presence and absence of 200 ng/mL of TRAIL.
Figure 7:
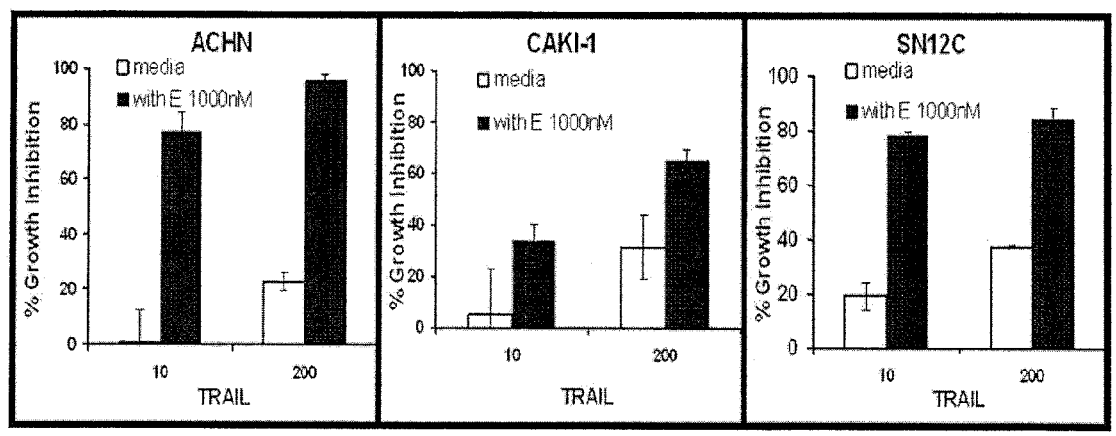
FIG. 7 depicts the percent growth inhibition of three different renal cancer cell lines in the presence of 1000 nM of withanolide E and either 10 ng/mL or 200 ng/mL of TRAIL.
Figure 8:
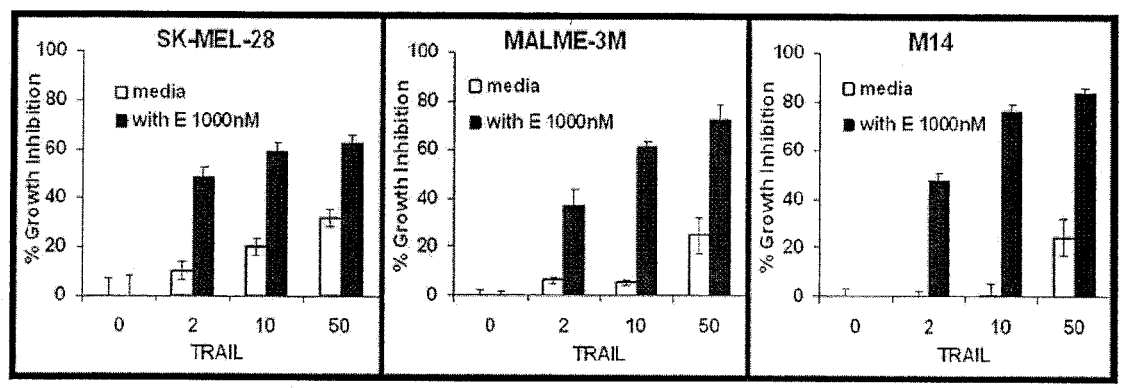
FIG. 8 depicts the percent growth inhibition of three different melanoma cell lines in the presence of 1000 nM of withanolide E and either 10 ng/mL or 200 ng/mL of TRAIL.
Figure 9:
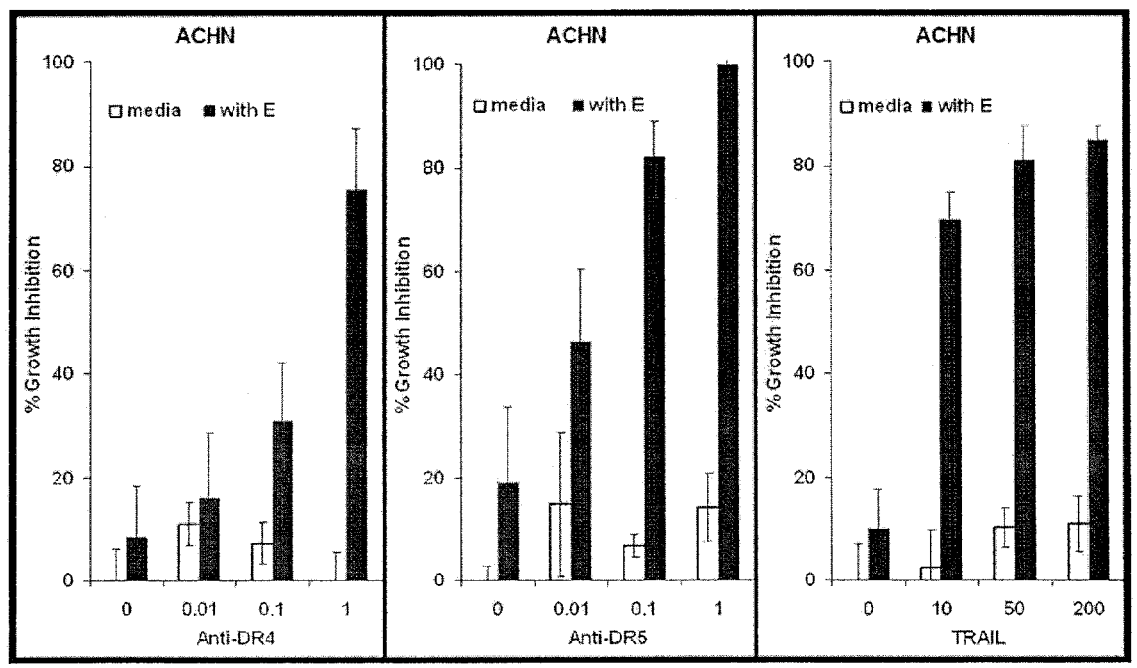
FIG. 9 depicts the sensitization by withanolide E of ACHN renal cancer cells to TRAIL, anti-DR4, and anti-DR5.

The Western blots determined using the above protocol for withanolide E is depicted in FIG. 5. As is apparent from the results set forth in FIG. 5, treatment of ACHN cells withanolide plus TRAIL resulted in the cleavage of caspase-8.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of synergistically enhancing the response of cancer cells in a mammal to treatment with a death receptor ligand, wherein the cancer cells are resistant to treatment with the death receptor ligand, which method consists essentially of administering to the mammal an effective amount of a compound selected from the group consisting of a cucurbitacin derivative of formula (I):

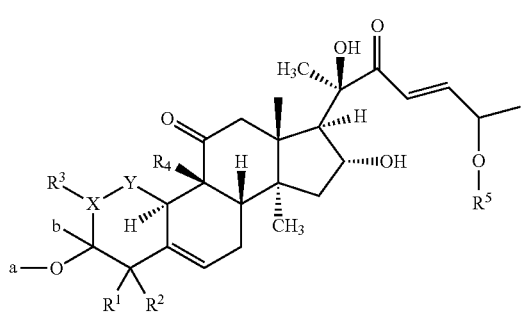

wherein $R^1$ and $R^2$ are independently hydrogen or $C_1$-$C_6$ alkyl,
wherein $R^3$ is hydrogen or OH,
wherein $R^4$ is methyl or $CH_2OH$,
wherein $R^5$ is hydrogen, $C_1$-$C_6$ alkylcarbonyl, or $C_6$-$C_{10}$ arylcarbonyl,
wherein a and b are both hydrogen or a-O—C-b forms a C=O,
wherein X—Y is $CHCH_2$ or C=CH,
with the provisos that (i) when $R^4$ is $CH_2OH$ and X—Y is $CHCH_2$, $R^3$ is hydrogen, and (ii) when $R^5$ is hydrogen and $R^3$ is OH, X—Y is C=CH,
a withanolide derivative of Formula (II):

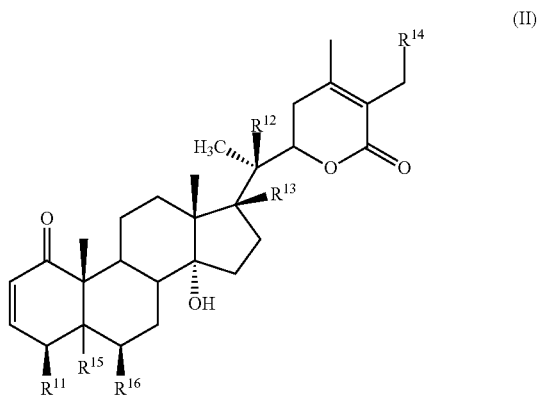

wherein $R^{11}$, $R^{12}$, $R^{13}$, and $R^{14}$, are independently hydrogen, OH, $C_1$-$C_6$ alkyloxy, or $C_1$-$C_6$ alkylcarbonyl, and wherein $R^{15}$ and $R^{16}$ are both OH or wherein $R^{15}$ and $R^{16}$ together form an epoxy ring, a compound of Formula (III):

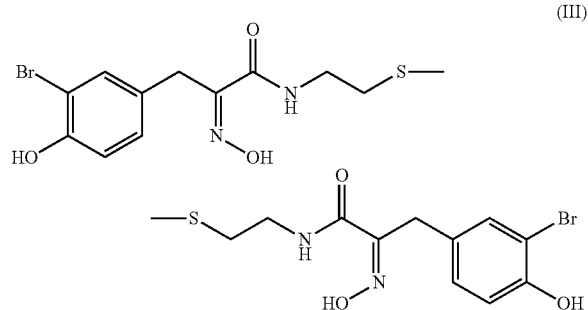

(III)

a compound of Formula (IV):

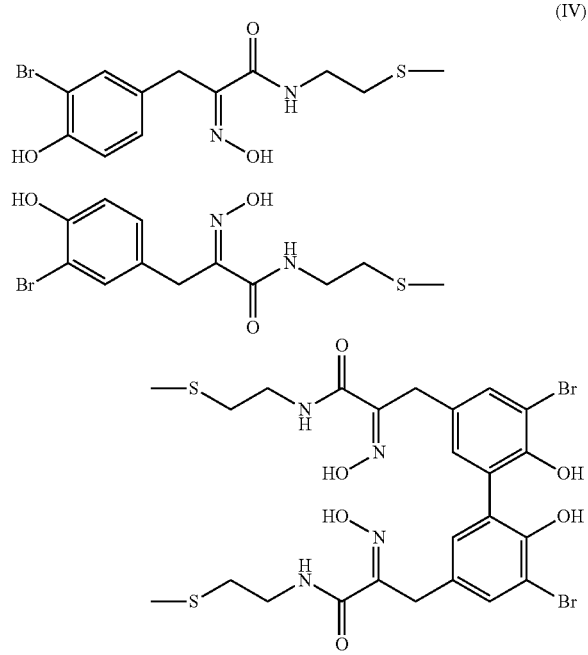

(IV)

and a compound of Formula (V):

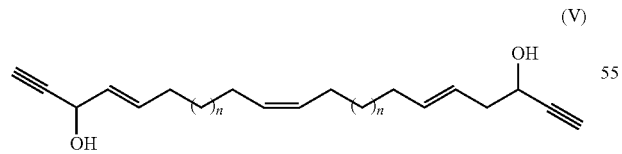

(V)

wherein n is an integer from 1 to 10, and administering an effective amount of a death receptor ligand, whereby a synergistic enhancement of the response is obtained.

2. The method of claim 1, wherein the compound is a cucurbitacin derivative selected from the group consisting of cucurbitacin B, cucurbitacin C, cucurbitacin E, and cucurbitacin I.

3. The method of claim 1, wherein the compound is a withanolide derivative which is withanolide E or withanolide S.

4. The method of claim 1, wherein the death receptor ligand binds to DR4 or DR5.

5. The method of claim 1, wherein the death receptor ligand is selected from the group consisting of TRAIL, TNF-α, FasL, an anti-DR4 antibody, and an anti-DR5 antibody.

6. The method of claim 5, wherein the death receptor ligand is TRAIL.

7. The method of claim 1, wherein the cancer cells are associated with a cancer selected from glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, multiple myeloma, mesothelioma, and melanoma, and combinations thereof.

8. A method of inducing apoptosis in cancer cells in a mammal that are resistant to treatment with a death receptor ligand, consisting essentially of administering to the mammal an effective amount of a cucurbitacin derivative of formula (I):

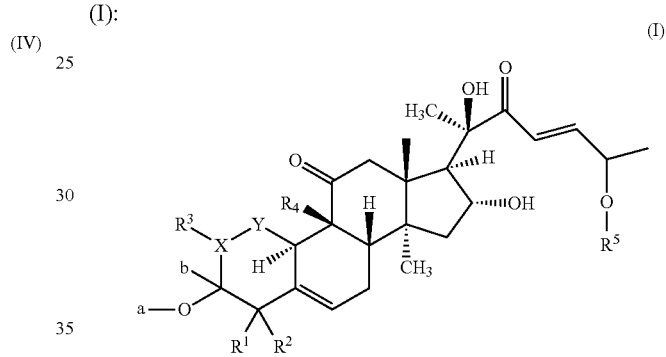

(I)

wherein $R^1$ and $R^2$ are independently hydrogen or $C_1$-$C_6$ alkyl, wherein $R^3$ is hydrogen or OH, wherein $R^4$ is methyl or $CH_2OH$, wherein $R^5$ is hydrogen, $C_1$-$C_6$ alkylcarbonyl, or $C_6$-$C_{10}$ arylcarbonyl, wherein a and b are both hydrogen or a-O—C-b forms a C=O, wherein X—Y is $CHCH_2$ or C=CH, with the provisos that (i) when $R^4$ is $CH_2OH$ and X—Y is $CHCH_2$, $R^3$ is hydrogen, and (ii) when $R^5$ is hydrogen and $R^3$ is OH, X—Y is C=CH, a withanolide derivative of Formula (II):

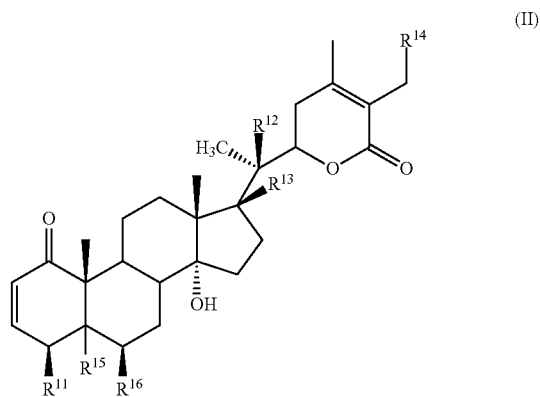

(II)

wherein $R^{11}$, $R^{12}$, $R^{13}$, and $R^{14}$, are independently hydrogen, OH, $C_1$-$C_6$ alkyloxy, or $C_1$-$C_6$ alkylcarbonyl,
and wherein $R^{15}$ and $R^{16}$ are both OH or wherein $R^{15}$ and $R^{16}$ together form an epoxy ring, a compound of Formula (III):

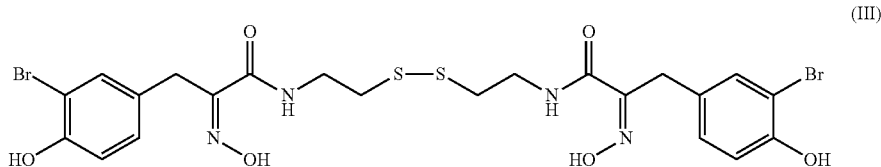 [SMILES: O=C(NCCSSCCNC(=O)/C(Cc1ccc(O)c(Br)c1)=N\O)/C(Cc1ccc(O)c(Br)c1)=N\O]

(III)

a compound of Formula (IV):

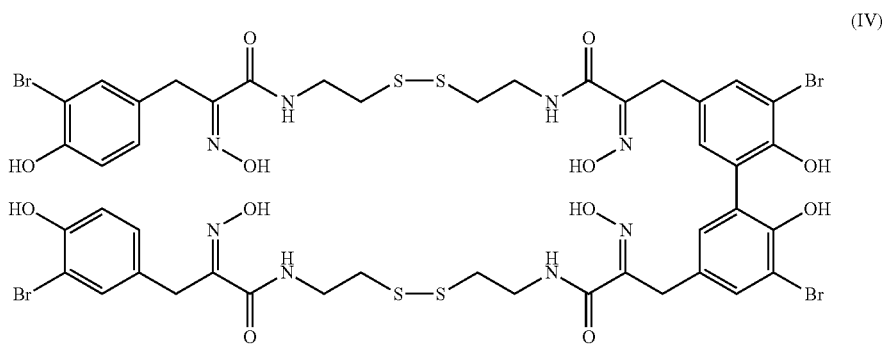 [SMILES: O=C(NCCSSCCNC(=O)/C(Cc1cc(Br)c(O)c(-c2cc(C/C(=N/O)C(=O)NCCSSCCNC(=O)/C(Cc3ccc(O)c(Br)c3)=N\O)cc(Br)c2O)c1)=N\O)/C(Cc1ccc(O)c(Br)c1)=N\O]

(IV)

and a compound of Formula (V):

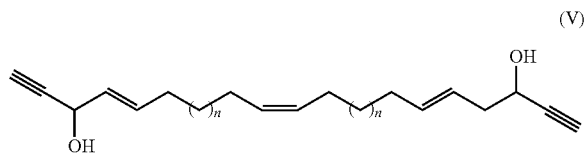

(V)

wherein n is an integer from 1 to 10,
and administering an effective amount of a death receptor ligand, whereby apoptosis is induced in the cancer cells.

9. The method of claim 8, wherein the cucurbitacin derivative is selected from the group consisting of cucurbitacin B, cucurbitacin C, cucurbitacin E, and cucurbitacin I, or a combination thereof.

10. The method of claim 8, wherein the withanolide derivative is withanolide E or withanolide S.

11. The method of claim 8, wherein the death receptor ligand binds to DR4 or DR5.

12. The method of claim 8, wherein the death receptor ligand is selected from the group consisting of TRAIL, TNF-α, FasL, an anti-DR4 antibody, and an anti-DR5 antibody.

13. The method of claim 12, wherein the death receptor ligand is TRAIL.

14. The method of claim 8, wherein the cancer cells are associated with a cancer selected from glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, multiple myeloma, mesothelioma, and melanoma, and combinations thereof.

* * * * *